(12) United States Patent
Lin

(10) Patent No.: US 7,125,250 B2
(45) Date of Patent: Oct. 24, 2006

(54) SCREW DEVICE FOR ORTHODONTIC TREATMENT

(76) Inventor: Cheng-Yi Lin, No. 190-1, WenHwa Rd., PanChiao, Taipei (TW)

(*) Notice: Subject to any disclaimer, the term of this patent is extended or adjusted under 35 U.S.C. 154(b) by 272 days.

(21) Appl. No.: 10/732,292

(22) Filed: Dec. 11, 2003

(65) Prior Publication Data

US 2004/0157187 A1  Aug. 12, 2004

Related U.S. Application Data

(63) Continuation-in-part of application No. 10/359,577, filed on Feb. 7, 2003, now Pat. No. 6,722,879.

(51) Int. Cl.
*A61C 7/00* (2006.01)
*A61C 8/00* (2006.01)

(52) U.S. Cl. ......................... 433/18; 433/174
(58) Field of Classification Search ................ 433/18, 433/172, 173, 174, 175, 176
See application file for complete search history.

(56) References Cited

U.S. PATENT DOCUMENTS

| 5,588,838 | A | * | 12/1996 | Hansson et al. | ............ 433/173 |
| 5,697,779 | A | * | 12/1997 | Sachdeva et al. | .............. 433/2 |
| 6,312,259 | B1 | * | 11/2001 | Kvarnstrom et al. | ........ 433/173 |
| 2002/0127510 | A1 | * | 9/2002 | Kyung et al. | ................. 433/18 |
| 2002/0182560 | A1 | * | 12/2002 | Park et al. | .................... 433/18 |

* cited by examiner

*Primary Examiner*—Cary E. O'Connor
(74) *Attorney, Agent, or Firm*—Troxell Law Office, PLLC

(57) ABSTRACT

A screw device for orthodontic treatment comprises a screw-body part, a platform part integrally formed with the screw-body part, and a head part. The head part is detachable from and exposed outside the screw-body part and is operatable to hook a spring (or rubber band) for orthodontic treatment. Since the head part is detachable, various types of head parts can be chosen to attach on the same platform part and screw-body part for performing different orthodontic treatments. Cost to manufacture the screw device is lower, and flexibility and convenience to use the screw device are higher. The external threads of the screw-body part are slightly loosened and tapered at a portion away from the platform part and relatively concentrated at another portion near to the platform part.

12 Claims, 14 Drawing Sheets

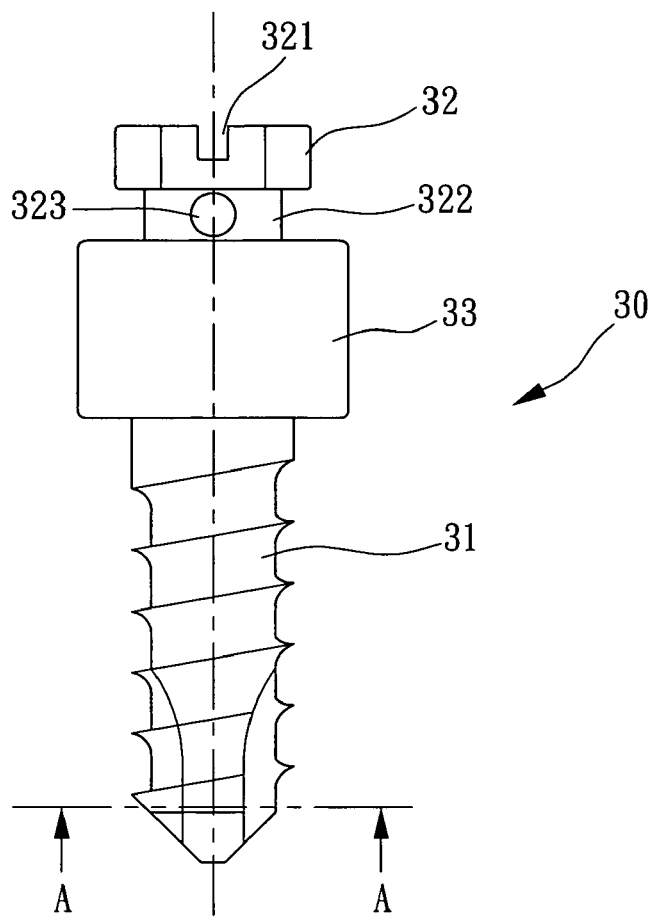
FIG. 4A
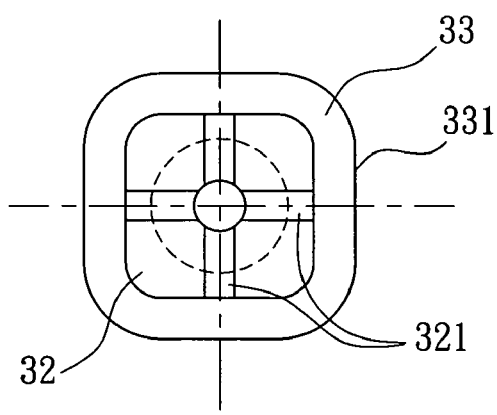 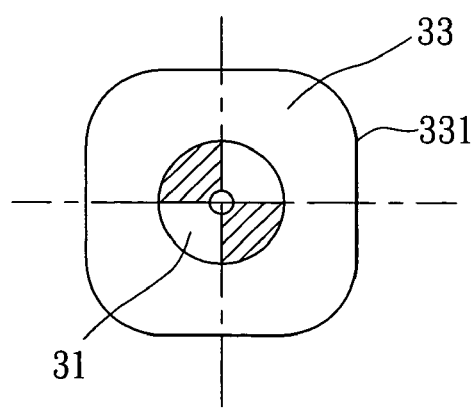
FIG. 4B              FIG. 4C

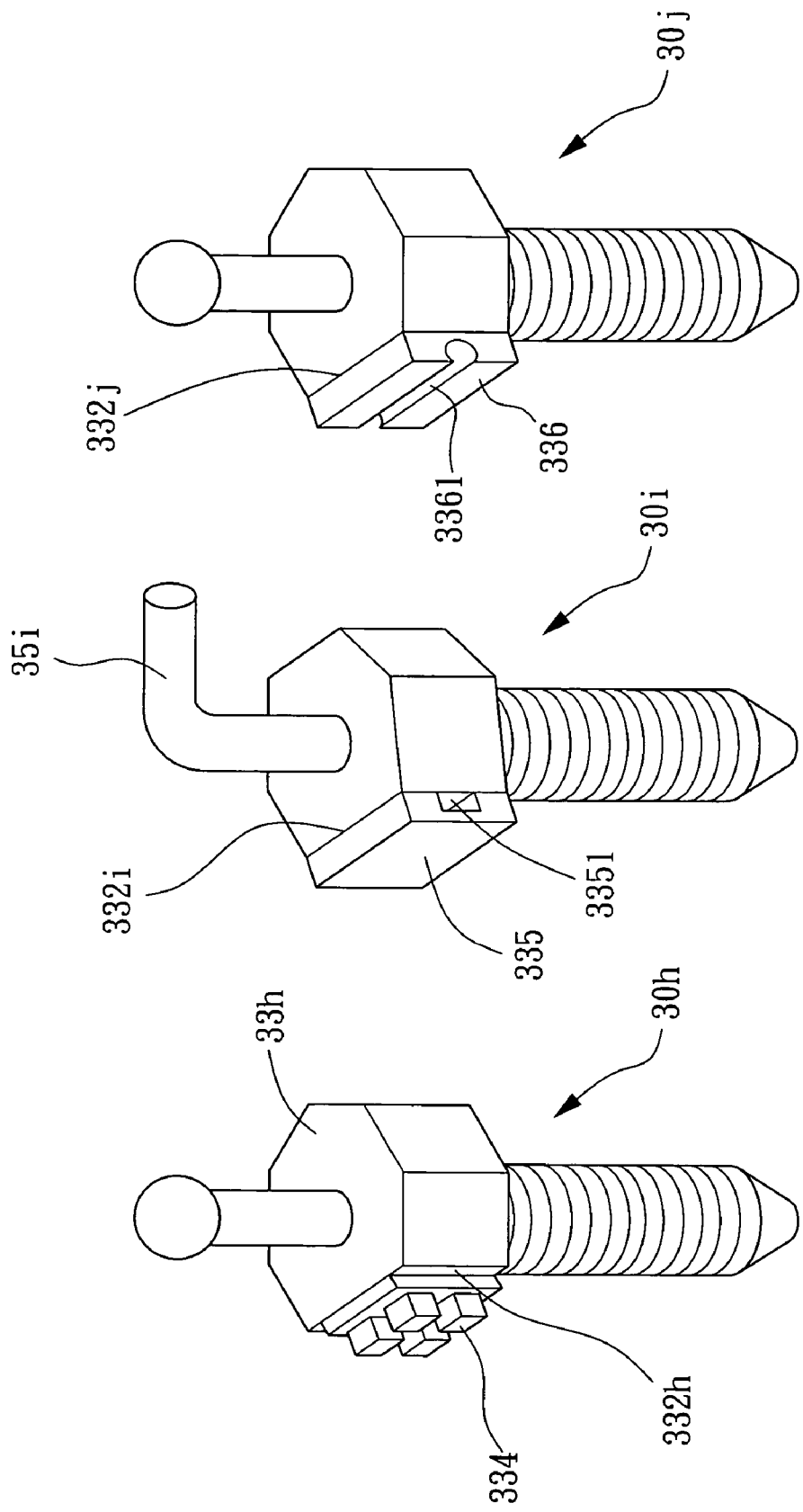

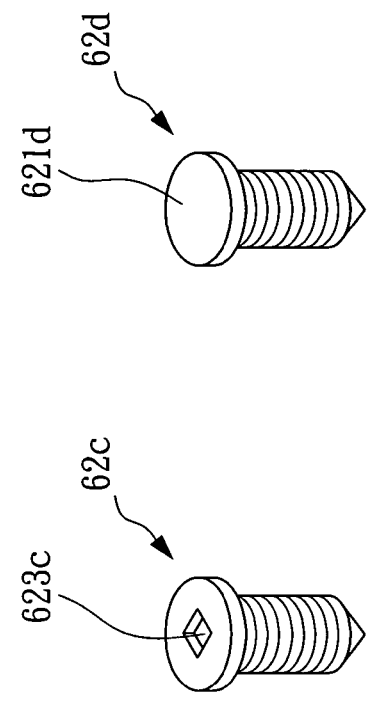
FIG. 16A
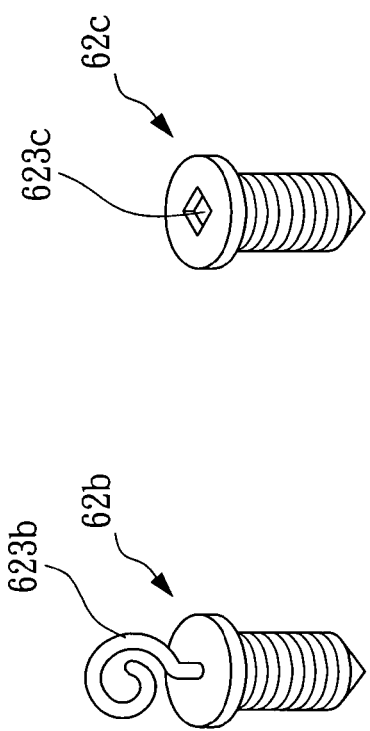
FIG. 16B
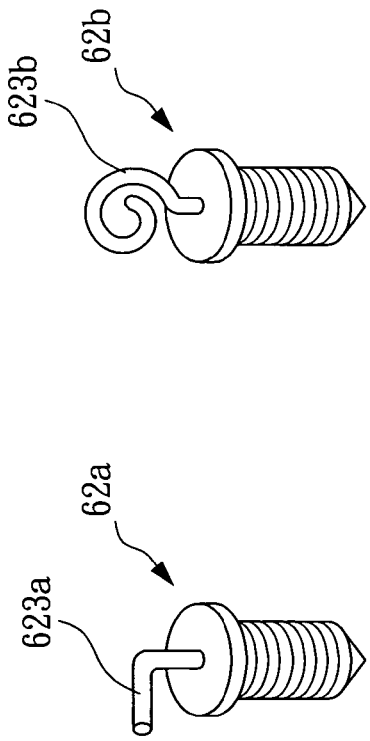
FIG. 16C
FIG. 16D
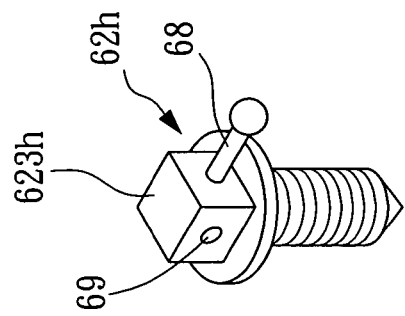
FIG. 16E
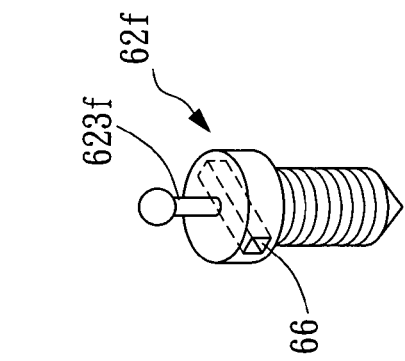
FIG. 16F
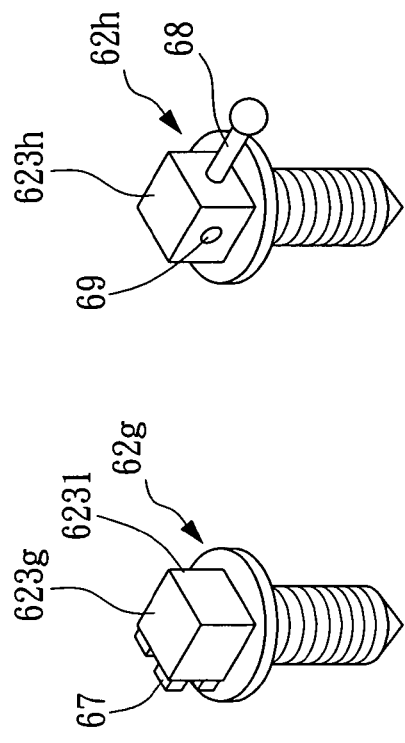
FIG. 16G
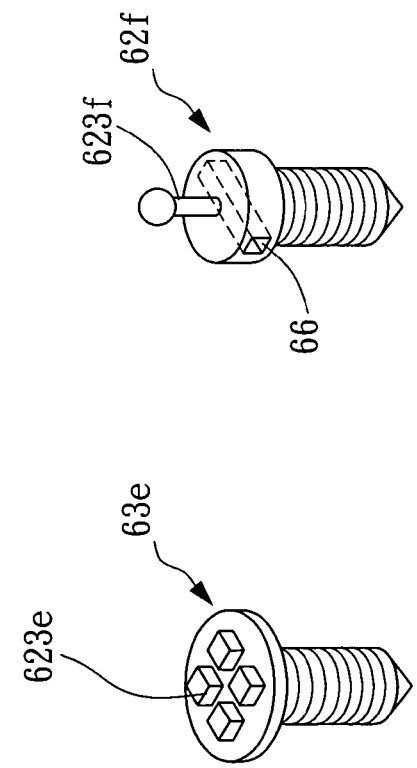
FIG. 16H

SCREW DEVICE FOR ORTHODONTIC TREATMENT

The invention relates to a screw device for orthodontic treatment, especially to a screw device that may be arranged in the maxilla (or mandible) and is capable of positioning the spring used for orthodontic treatment and accommodating the orthodontic archwire. This application is a continue-in-part (CIP) application of U.S. patent application Ser. No. 10/359,577 filing date Feb. 7, 2003 now U.S. Pat. No. 6,722,879.

FIELD OF THE INVENTION

BACKGROUND OF THE INVENTION

As shown in FIG. 1, in a conventional orthodontic treatment process, after part of the maxilla (or mandible) 10 is cut off or a tooth 12 is pulled out (usually not the incisor), the tooth 12 or the maxilla (or mandible) 10 is pulled and dragged by an orthodontic archwire 13 after the operation for helping the maxilla (or mandible) 10 to heal over or correcting the position of the tooth 12. In order to maintain the position of the orthodontic archwire 13 relative to the tooth 12, it is usually to apply several orthodontic brackets 14 adhered onto the tooth 12, and each orthodontic bracket 14 is arranged with slot 141 for providing an accommodation for the orthodontic archwire 13. The width and the depth of the slot 141 must be slightly larger than the diameter of the orthodontic archwire 13 such that, not only may the orthodontic archwire 13 be appropriately glided along the extensive direction of the slot 141, but also may the orthodontic archwire 13 be kept from being dropped out of the slot 141.

As known in the prior arts, in order to provide a pulling-and-dragging force to the orthodontic archwire 13, a screw 20 is screwed on a maxilla (or mandible) 10 at the adjacency of a molar 121, then a spring 15 or rubber band is further connected between the screw 20 and the end of the orthodontic archwire 13 for providing an appropriate pulling-and-dragging force. Since the end of this kind of spring 15 used specially for orthodontic treatment in current market is all arranged with a hook ring 151 so, for the connection between the spring 15 and the end of the orthodontic archwire 13, the end of the orthodontic archwire 13 just may be bent into a hook structure 131, then it can be easy to fit the hook ring 151 of the spring 15 into the hook structure 131 of the end of the orthodontic archwire 13, such that both connection is completed. Relatively, the connection between the spring 15 and the screw 20 is more difficult relatively.

As shown in FIG. 2 and FIG. 3, since the screw 20 currently applied for orthodontic treatment is all belonged to the common screw 20 as shown in FIG. 2 and FIG. 3, so the materials used for the screw 20, orthodontic bracket 14, and orthodontic archwire 13 are usually pure titanium alloy or stainless steel, those which are harmless to the human body. The screw 20 is commonly comprised of two parts: the head part 21 and the screw-body part 22. A general screw head groove 211 is then arranged on the head part 21 for providing a securing operation for a screwdriver (not shown in the figure). Usually, the dimension of the head part 21 is the widest part along the entire screw 20. Further, the diameter of the head part 21 is usually larger than the inner diameter of the hook ring 151 of the end of the spring 15, such that it is impossible for the spring to be hooked and hanged on the screw 20 directly. Therefore, for the current prior arts, an additional ligature wire 16 is used for tying the end of the spring 15 onto the screw-body part of the screw 20. However, such kind of method has caused several shortcomings as follows:

(1) It is difficult to operate. Since the head part 21 of the screw 20 is larger than the hook ring 151 of the spring 15, so it is impossible for the spring to be hooked and hanged on the screw 20 but, if the diameter of the head part 21 of this prior screw 20 is designed to be smaller than the hook ring 151 of the spring 15, then it will be much more easier for the spring 15 to be dropped off from the screw 20 to cause further inconvenience. Therefore, the prior arts that still use additional ligature wire 16 for tying the spring 15 and the screw 20 not only cause inconvenient in operation, but also cause difficulties for a less-experienced doctor to approach such kind of operation.

(2) It is easy for the spring 15 and the ligature wire 16 to impinge the gingiva 11. Since the ligature wire 16 is tied on the screw-body part 22 of the screw 20, so the ligature wire 16 and the spring 15 will be sometimes abutted against the gingiva 11 and irritate it. Not only will the user feel uncomfortable, but also may it sometimes hurt the gingiva 11 or reduce the healing-over speed of the wounds after operation.

(3) It is easy loosening for the screw 20. Since the screw-body part 22 of the screw 20 has a partial length that must be left in advance for tying the ligature wire 16 so, when the screw 20 is being driven tightly, it is impossible to screw the screw-body part 22 of the screw 20 completely into the maxilla (or mandible) 10 to make its head part 21 abutted smoothly against the maxilla (or mandible) 10. Contrarily, the head part 21 of the screw 20 must be kept an appropriate distance with the maxilla (or mandible) 10 for proceeding the operation of tying the ligature wire 16. In such way, the pulling-and-dragging force between the spring 15 and the ligature wire 16 will create a torque to the head part 21 of the screw 20, so it is easy to cause the screw 20 to loosen or even to drop off and break off.

(4) The gingiva 11 will be ugly after being healed over. Since the tissue of the gingiva 11 will be sometimes abutted against the screw 20 to grow during the healing procedure and there is a lack of appropriate guidance and restriction, so the surface of the gingiva 11 is uneven and ugly after being healing over.

(5) It only has a single function. This kind of prior screw 20 only can be applied in tying the ligature wire 16 for connecting the spring 15, neither does it have any other function, nor is it possible for providing an accommodation for the orthodontic archwire 13.

U.S. Pat. No. 4,988,292 discloses an abutment for orthodontic anchorage to a dental implant fixture. It comprises an endosseous implant fixture which is fixed in the lower jaw at the site of a missing molar for supporting an abutment for orthodontic anchorage. The abutment and the fixture are connected by a bolt in a detachable manner. However, the abutment of U.S. Pat. No. 4,988,292 does not provide the function of spring hooking. Even if someone tries to hook the spring on the abutment, the spring will be prone to impinge the gingival as previously illustrated. In addition, the fixture is prone to loose since it has identical outer threads and identical outer diameter throughout the entire fixture.

U.S. Pat. No. 5,836,768 discloses a fastening device for fixing orthodontic apparatuses on a dental implant. It comprises an implant which is fixed in the jaw bone, an anchoring screw screwed within an axially arranged threaded bore in the implant, and an occlusal screw located inside the threaded bore and engaged with the anchoring screw. None part of the occlusal screw nor anchoring screw is exposed outside the implant, such that they cannot be used for spring hooking. Even if the spring can be tied (not hook) on a bracket of U.S. Pat. No. 5,836,768, the spring will be prone to impinge the gingival. In addition, the implant is prone to loose since it has identical outer threads and identical outer diameter.

U.S. Pat. No. 5,921,774 discloses a supporting body for use in orthodontic appliance. It comprises a supporting body to be fixed in the jaw bone, an abutment formed with an arm at a side surface thereof, and a male screw for screwing and fixing the abutment onto the top of the supporting body. Since the screw is an independent element and is screwed from a top side of the abutment, therefore the arm can only be form at the side surface of the abutment, and thus the application and flexibility thereof are limited. In addition, the device disclosed by U.S. Pat. No. 5,921,774 comprises at least three elements (e.g., supporting body, abutment and male screw). Not only the cost to manufacture is higher, but also is more complex to use. Moreover, the supporting body is prone to loose since it has identical outer threads (or no threads at all) and identical outer diameter throughout the entire supporting body.

Other prior art, such like U.S. Pat. No. 6,241,516, U.S. Pat. No. 5,071,345, and US Pub. No. 2002/0127510. None of them has been disclosed a screw device which comprises a screw-body part, a platform part and a head part which is detachable from and exposed outside the platform part (or screw-body part) and is operatable to hook the spring for orthodontic treatment.

As known from above description, the prior arts that are used for orthodontic treatment currently still have many shortcomings to be further improved urgently.

SUMMARY OF THE INVENTION

The main objective of the invention is to provide an improvement for a screw device for orthodontic treatment. The screw device in accordance with the present invention comprises a screw-body part, a platform part and a head part. The head part is detachable from and exposed outside the platform part and is operatable to hook the spring for orthodontic treatment. Since the head part is detachable, user can design and apply various types of head parts to attach on the same platform part (and screw-body part) for performing different orthodontic treatments. Cost to manufacture various types of the screw devices is lower, and flexibility and convenience to use the screw devices are higher.

Another objective of the invention is to provide a screw device for orthodontic treatment. The screw device complying with this object comprises a specially designed screw-body part. The external threads of the screw-body part are slightly loosened at a portion away from the platform part and relatively concentrated at another portion near to the platform part, such that it can be tightly fastened into the bone for avoiding any looseness.

The further objective of the invention is to provide a screw device for orthodontic treatment. The screw device comprises a specially designed screw-body part which is tapered at a section away from the platform part for around 2~10 degrees of tapering angle, such that it can be tightly fastened into the bone for avoiding any looseness.

For further understanding the objects, the characteristics, and the functions of the structures of the present invention, a detailed description matched with corresponding drawings are presented as follows.

BRIEF DESCRIPTION OF THE DRAWINGS

FIGS. 4A, 4B, and 4C are respectively a front view, top view, and A—A sectional view for the first preferred embodiment for the screw device according to the invention for orthodontic treatment.

FIG. 11 is the eleventh preferred embodiment for the screw device according to the invention for orthodontic treatment.

FIG. 12 is the twelfth preferred embodiment for the screw device according to the invention for orthodontic treatment.

FIG. 13 is the thirteenth preferred embodiment for the screw device according to the invention for orthodontic treatment.

FIG. 16A~16H are some preferred embodiments of the head parts which can be screwed onto the screw-body part of the present invention.

DETAILED DESCRIPTION OF THE INVENTION

Figure 1:
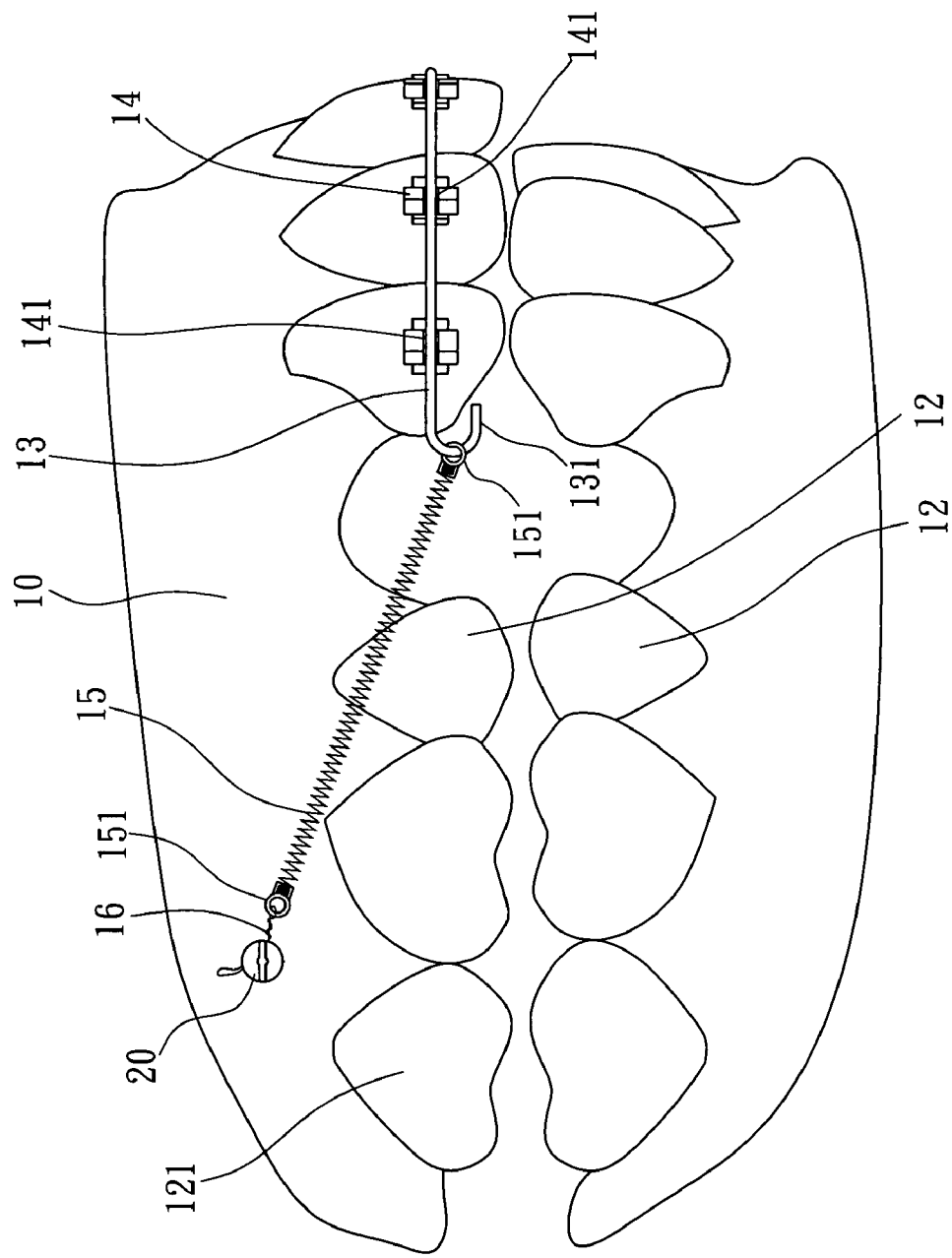
FIG. 1 is an embodiment illustration for a screw device, according to the prior arts, arranged in the mouth for orthodontic treatment.
Figure 2:
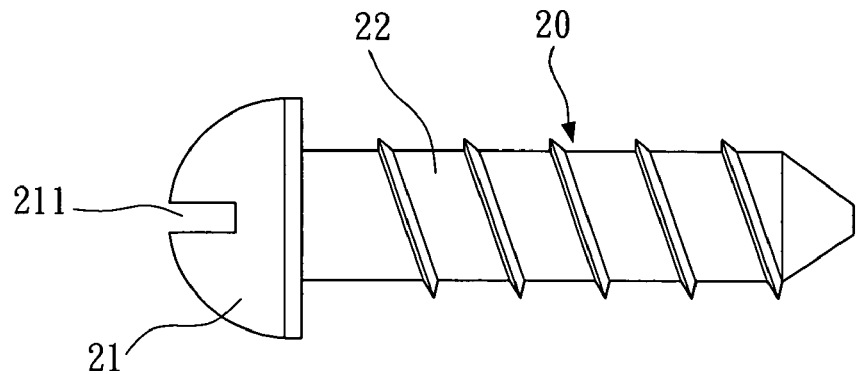
FIG. 2 is a front view for a screw according to the prior arts for orthodontic treatment.
Figure 3:
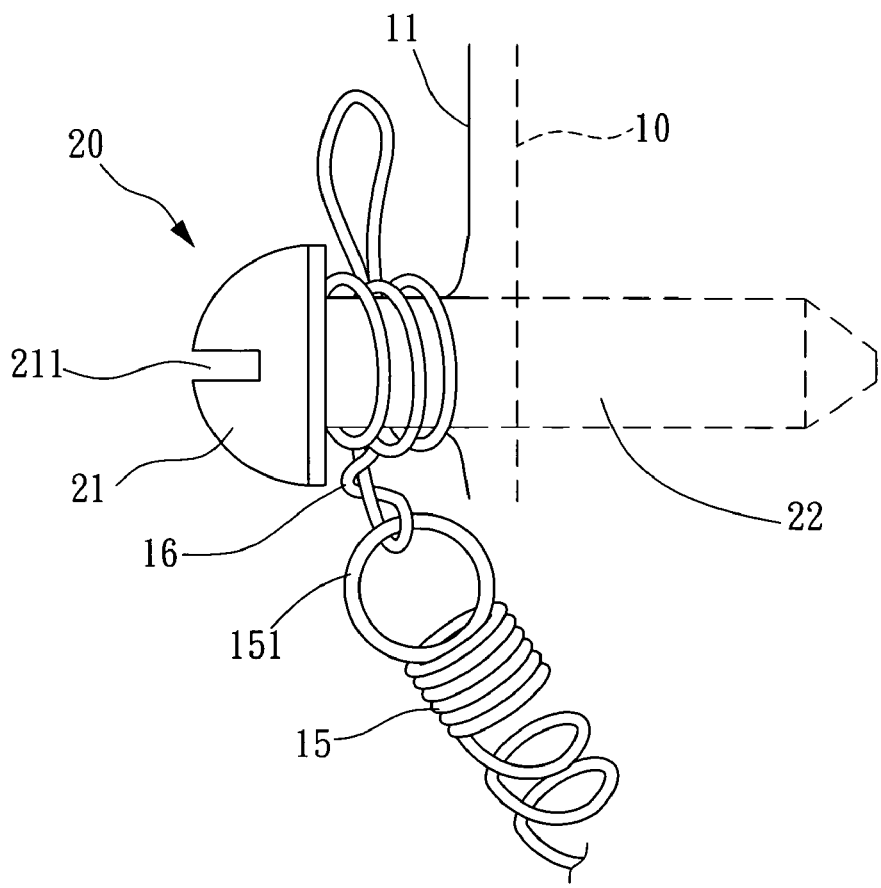
FIG. 3 is an illustration for tying and connecting an additional ligature wire with the spring and the screw according to the prior arts for orthodontic treatment.

The elements described thereinafter, such as: maxilla (or mandible) 10, gingiva 11, tooth 12, orthodontic archwire 13, orthodontic bracket 14, and spring 15 (or rubber band) for orthodontic treatment etc., and their relative position arranged in the mouth are all similar to the prior arts shown in FIG. 1 and they are not the technical characteristic of the invention, so they will be given same element names and referential numbers and their detailed composition, arrangement position, and function are not described herein repetitiously. One thing is worth mentioning: although the embodiment of the prior arts shown in FIG. 1 only depicts an embodiment that a correction device is arranged on the outside of the upper jaw, however, it may also be arranged on the outside or inside surface of maxilla (or mandible).

Figure 5:
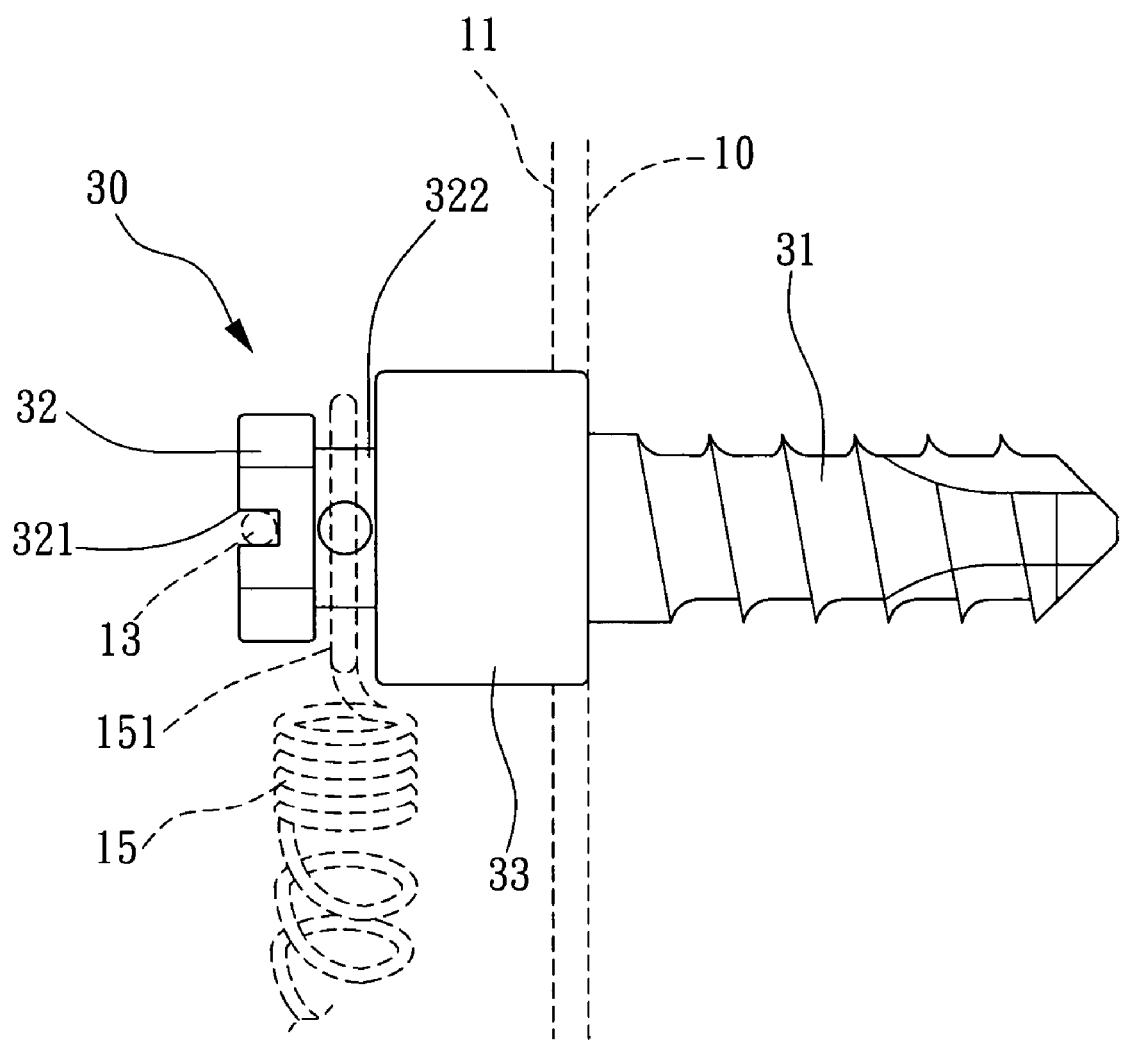
FIG. 5 is an illustration for a preferred embodiment for the screw device according to the invention for orthodontic treatment in matching with the spring and the orthodontic archwire, both which are arranged on the maxilla (or mandible) for orthodontic treatment.

Please refer to FIG. 4A to FIG. 4C, which are respectively a front view, top view, and A—A sectional view for a preferred embodiment for the screw device for orthodontic treatment according to the invention. FIG. 5 is an illustration for a preferred embodiment for the screw device 30 for orthodontic treatment according to the invention in matching with the spring 15 and the orthodontic archwire 13, both which are arranged on the maxilla (or mandible) 10 for orthodontic treatment.

As shown in FIG. 4A, FIG. 4B, FIG. 4C, and FIG. 5, in the preferred embodiment of the invention, the screw 30 for orthodontic treatment is integrally comprised of a screw-body part 31 of pillar shape, a head part 32, and a platform part 33. The materials of the screw 30 according to the invention may be titanium alloy or stainless steel or other rigid materials that are harmless to human body. The screw may be manufactured by a method of integral formation, or only the screw-body part 31 and the platform part 33 are manufactured integrally first, then the head part 32 is manufactured separately, and the head part 32 is then welded or glued onto the platform 33.

The screw-body part 31 is located at one side of the screw 31. The screw-body part 31 of pillar shape is extended an appropriate length along an axis and has a first diameter in the radial direction. On the screw-body part 31, there is screw tooth arranged for being screwed into the maxilla (or mandible) 10. The head part 32 is located at another side of the screw 30 corresponding to the screw-body part 31. The head part 32 has a first width in the said radial direction. The first width is usually smaller than the inner diameter of the hook ring 151 of the spring 15 for providing the hook ring 151 to be fitted directly into the head part 32 of the screw 30. In a preferred embodiment, the head part 32 may be designed in similarity to the prior orthodontic bracket 14 to have a structure of slot 321 extending in radial direction. The width and the depth included in the dimension of the slot 321 are preferably slightly larger than the diameter of the orthodontic archwire 13. General speaking, there are two kinds of dimension for the slot 141 of the prior current orthodontic bracket 14 and the slot 321 of the screw 30 of the invention: one is that the width and the depth are 0.022 inch and 0.028 inch respectively, and the other combination is 0.018 inch and 0.025 inch. Accommodating the orthodontic archwire 13 into the slot 321 of the head part 32 of the screw 30 will make the screw 30 of the invention provide a function similar to that of the prior orthodontic bracket 14 (as shown in FIG. 5).

The platform part 33 is connected between the screw-body part 31 and the head part 32, and the platform part 33 has an appropriate thickness in the axial direction and has a second width in the radial direction. Preferably, the second width is larger relatively. That is, the second width of the platform part 33 is larger than the first width of the head part 32, the first diameter of the screw-body part 31, and the inner diameter of the hook ring of the spring 15. A neck part 322 is also formed at the connection place of the head part 32 and the platform part 33. At least one radial width of the neck part 322 is smaller than the first width of the head part 32 to make the neck part 322 become a part with narrowest width at a location relatively between the head part 32 and the platform part 33. The hook ring 151 of the spring 15 may be directly fitted into the head part 32, and be hooked and secured at the position of the neck part 322. One end of the spring 15 is connected to and secured on the screw 30 device. The thickness of the platform part 33 may keep the spring 15 from being abutted against the screw-body part 31.

Two side planes, of the platform part 33, adjacent to the screw-body part 31 and the head part 32 in the axial direction, are the planes that each has relatively larger area. Thereby, since the side plane, adjacent to the neck part 322, is wider than the diameter of the hook ring 151 of the spring 15, so it will become a working platform for facilitating a doctor in the operation of hooking and hanging the spring 15. Not only is the operation very easy, but also may the spring 15 be directly fitted, hooked, and hanged at the neck part 322 of the screw 30 completely without any worry of being dropped off, so it is absolutely unnecessary to apply additional ligature wire for tying the spring 15. Relatively, the side plane, at the outer contour of the platform part 33, having relatively larger area and smooth surface, will be beneficial in guiding the tissue of the gingiva 11 to grow during the healing over procedure of the wounds after operation, such that the surface of the gingiva 11 after being healing over is more even and beautiful. Furthermore, when the screw-body part 31 of the screw 30 of the invention is almost completely screwed into the maxilla (or mandible) 10, the lower side surface, of the platform part 33, at the adjacency of the screw-body part 31, will be approximately abutted against the surface of the maxilla (or mandible) 10. At this time, the platform part 33, of relatively larger area, will be able to keep the screw 30 from incurring loose phenomenon because of being forced. Of course, we may also choose that the screw-body part 31 is not completely screwed into the maxilla (or mandible) 10 and a gap is still left.

In this preferred embodiment, at least one penetration hole 323 of axial direction may further be arranged in the neck part 322 at the jointed place of the head part 32 and the platform part 33. The inner diameter of the penetration hole 323 may be larger than the diameter of the wire loop of the spring 15 or larger than the diameter of the orthodontic archwire 13. In another embodiment not shown in the figure, the wire of the end of the spring 15 (or the end of the orthodontic archwire 13) may be directly fitted into the penetration hole 323 of the neck part 322 and wound around the outer contour of the neck part 322, such that an objective for securing and positioning the end of the spring 15 (or the end of the orthodontic archwire 13) to the screw 30 is achieved.

In this preferred embodiment, since the head part 32 of the screw 30 is designed as a slot 321 structure similar to the orthodontic bracket 14 capable of accommodating the orthodontic archwire 13, so a common screwdriver is inappropriate for screwing the screw 30 of the invention into the maxilla (or mandible) 10. If a common traditional screwdriver is used directly for screwing the screw 30 of the invention, then it is easy to deform or wear out the slot 321 on the head part 32, such that the slot 321 is no more appropriate for accommodating the orthodontic archwire 13. Therefore, the invention designs the outer contour in the radial direction of the platform 33 as a polygon contour 331 of a noncircular shape, such as the contour structure similar to a square and shown in FIG. 4B and FIG. 4C. This structure may be matched with an external screwdriver 40 specially designed for the screw 30 of the invention.

Figure 6C:
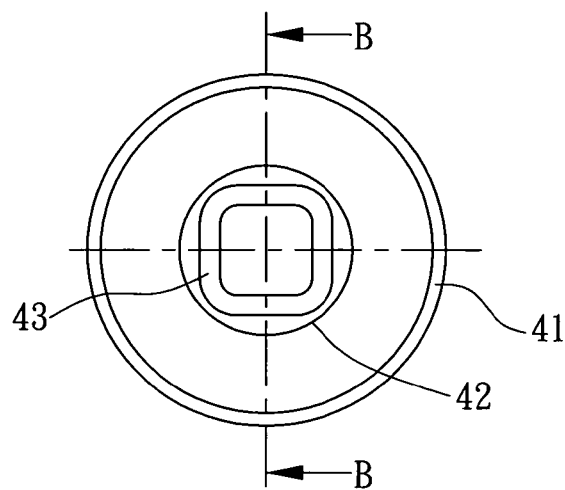
FIGS. 6A, 6B, and 6C are respectively a front view, B—B sectional view, and top view for a preferred embodiment for the screw device according to the invention for orthodontic treatment in matching with a screwdriver.
Figure 6A:
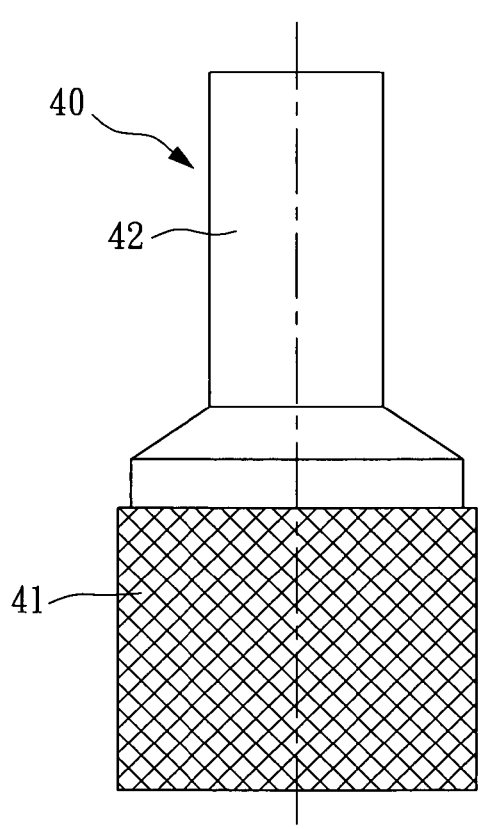
Figure 6B:
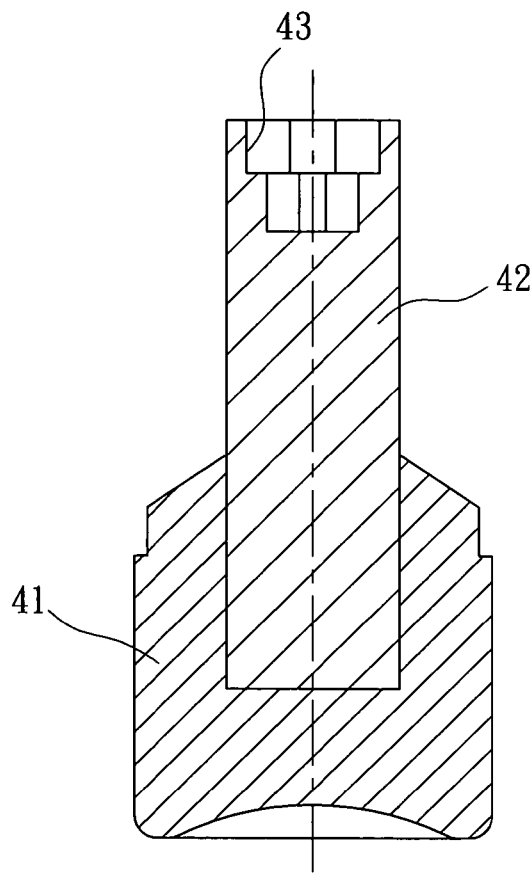

Please refer to FIGS. 6A, 6B, and 6C, which are respectively a front view, B—B sectional view, and top view for a preferred embodiment for the screw 30 device for orthodontic treatment according to the invention in matching with a screwdriver 40. The screwdriver 40 has a handle part 41 available for the user to grip, a rotation rod 42 extended out an appropriate distance from one side of the handle part 41, and a polygon recession seat 43 indented inwardly and arranged to the end of the rotation rod 42. The shape and the contour of the polygon recession seat 43 is just corresponded to and matched with the outer contour of the polygon contour 331 of the platform part 33. The recession depth and the shape of the polygon recession seat 43 may at least accommodate the head part 32 to make the polygon recession seat 43 inset onto the platform part 33. Gripping and rotating the handle part 41 may screw the screw 30 into or off the maxilla (or mandible) 10.

Figure 7:
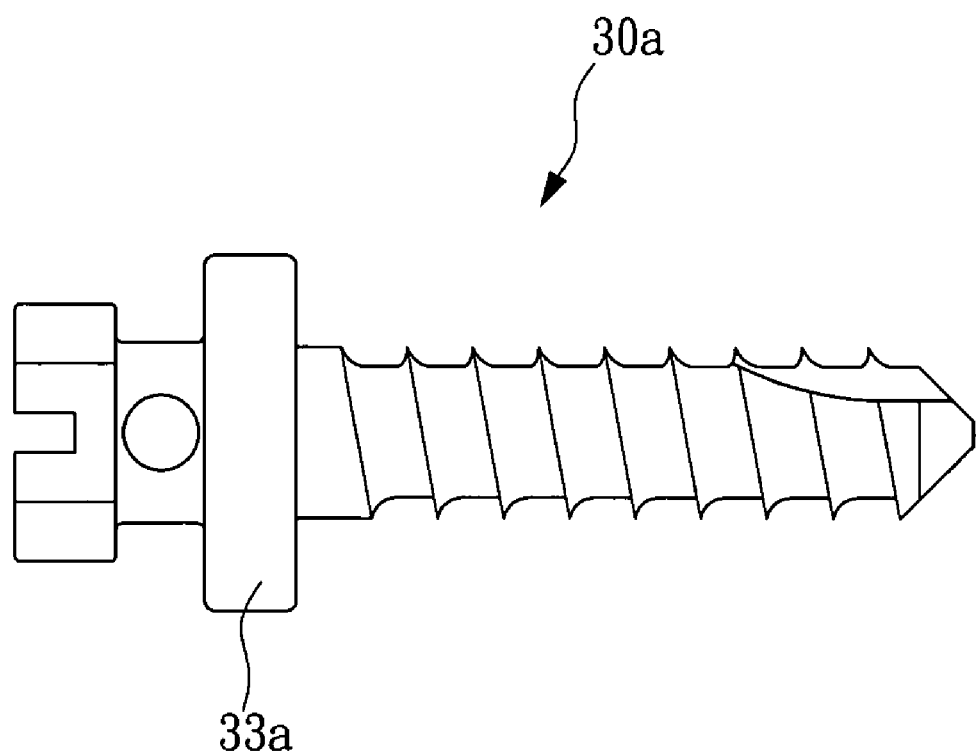
FIG. 7 is the second preferred embodiment for the screw device according to the invention for orthodontic treatment.

Please refer to FIG. 7, which is another preferred embodiment for the screw 30a device according to the invention for orthodontic treatment. In this preferred embodiment, most elements of the screw 30a are same as those shown in FIG. 4A, so a repetitious description is not presented herein any more. The only different point is that the platform part 33a of the screw embodiment shown in FIG. 7 has a relatively thinner thickness for being adapted to different requirement, for example, when the mouth's mucous membrane of the patient to be corrected is thinner.

Figure 8A:
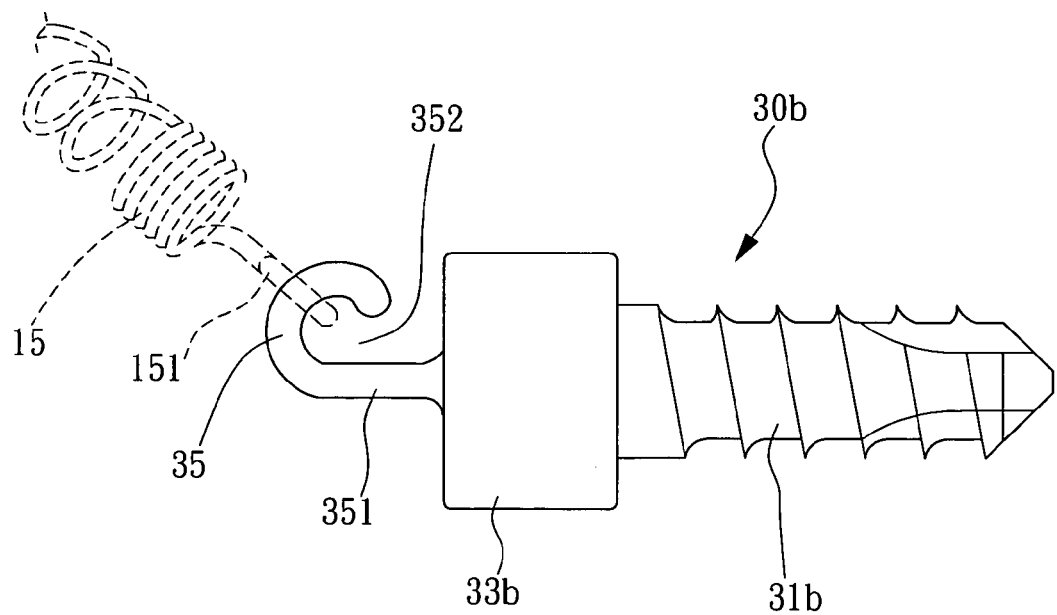
FIG. 8A is the third preferred embodiment for the screw device according to the invention for orthodontic treatment.

Please refer to FIG. 8A, which is a further preferred embodiment for the screw 30b device according to the invention for orthodontic treatment. In this preferred embodiment, most elements of the screw 30b are same as those of the embodiment shown in FIG. 4A. The screw 30b also has a screw-body part 31b, a platform part 33b, a head part 35, and a neck part 351. The different point of the screw 30b shown in FIG. 8A is that, in this embodiment, instead of showing a slot as a orthodontic bracket structure, the head part 35 of the screw 30b is designed extensively as a hook-shaped structure. In this embodiment, the head part 35 is wound by a wire to be shown as an arc shape for constituting the hook-shaped structure, and the arc-shaped wire is wound approximately to 180 degree to 300 degree for leaving a gap 352 for providing the hook ring 151 of the spring 15 to be fitted in. When the hook ring 151 of the spring 15 is hooked directly with the head part 35, the hook-shaped structure may keep the spring 15 from being dropped off.

Figure 8B:
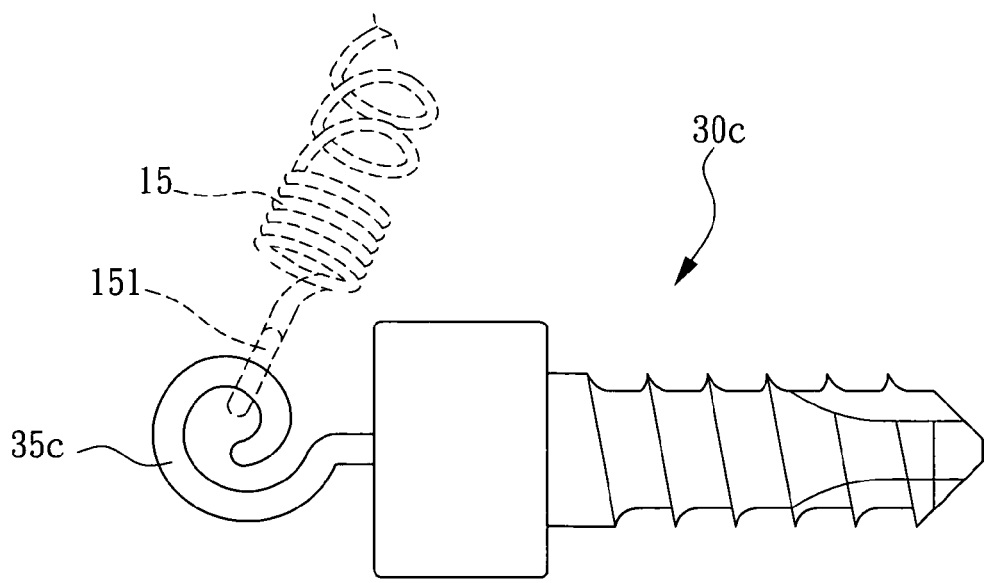
FIG. 8B is the forth preferred embodiment for the screw device according to the invention for orthodontic treatment.

Please refer to FIG. 8B, which is a further preferred embodiment for the screw 30c device according to the invention for orthodontic treatment. In this preferred embodiment, most elements of the screw 30c are same as those of the embodiment shown in FIG. 8A, so a repetitious description is skipped herein. The only one different point is that the head part 35c of the screw 30c shown in FIG. 8B is formed as a swirl-shaped structure by an arc-shaped wire wound at least 360 degrees, so it has better functions for the hook ring 151 of the spring 15 to be positioned and secured, no matter with which angle the spring is connected to the head part 35c of this screw 30c, it still can be kept from loosening off.

Figure 9B:
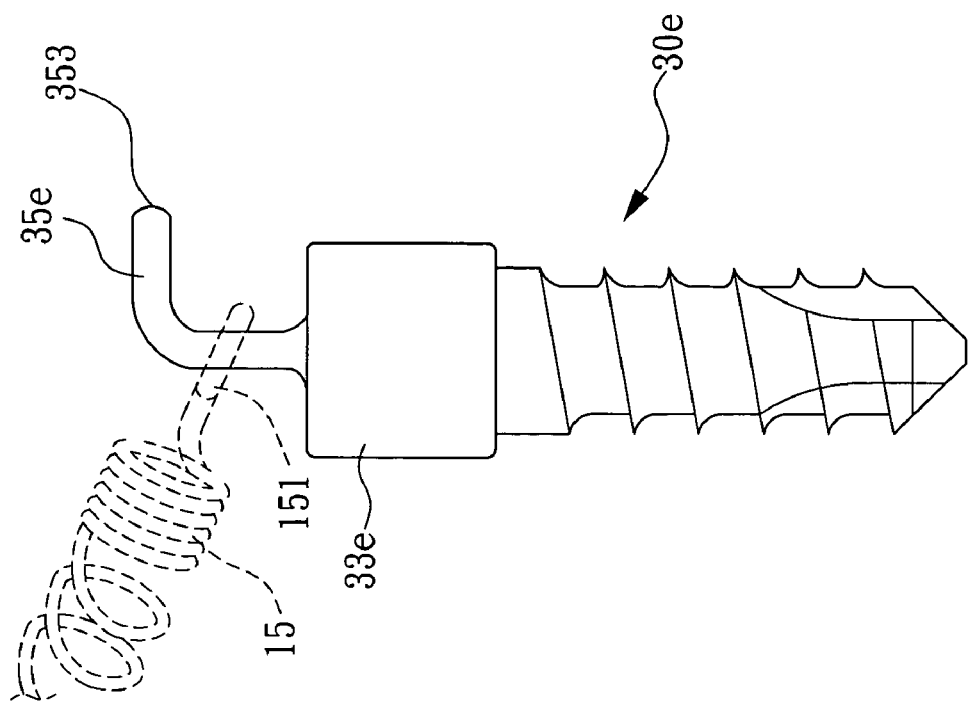
FIG. 9B is the sixth preferred embodiment for the screw device according to the invention for orthodontic treatment.
Figure 9A:
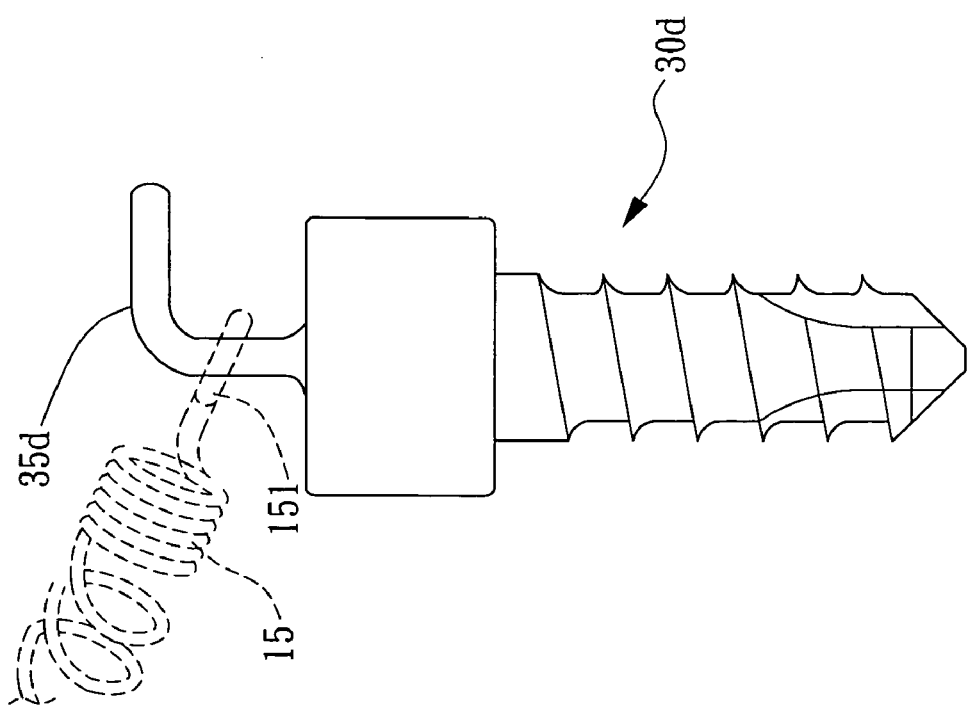
FIG. 9A is the fifth preferred embodiment for the screw device according to the invention for orthodontic treatment.

Please refer to FIG. 9A, which illustrates the fifth preferred embodiment for the screw device according to the invention for orthodontic treatment. In this preferred embodiment, most elements of the screw 30d are same as those of the embodiment shown in FIG. 8A, so a repetitious description is skipped herein. The only one different point is that the head part 35d of the screw 30d shown in FIG. 9A is formed as a reversed L-shaped structure by a wire bent at 90 degrees, so it has the benefit of being simple structure and easy to be manufactured.

FIG. 9B is the sixth preferred embodiment for the screw device according to the invention for orthodontic treatment. In this preferred embodiment, most elements of the screw 30e are same as those of the embodiment shown in FIG. 9A, so a repetitious description is skipped herein. The only one different point is that the platform part 33e of the screw 30e is narrower than which of the screw 30d shown in FIG. 9A. Moreover, the leading end 353 of the head part 35 is extending out of the outer contour of the narrowed platform part 33e.

Figure 9C:
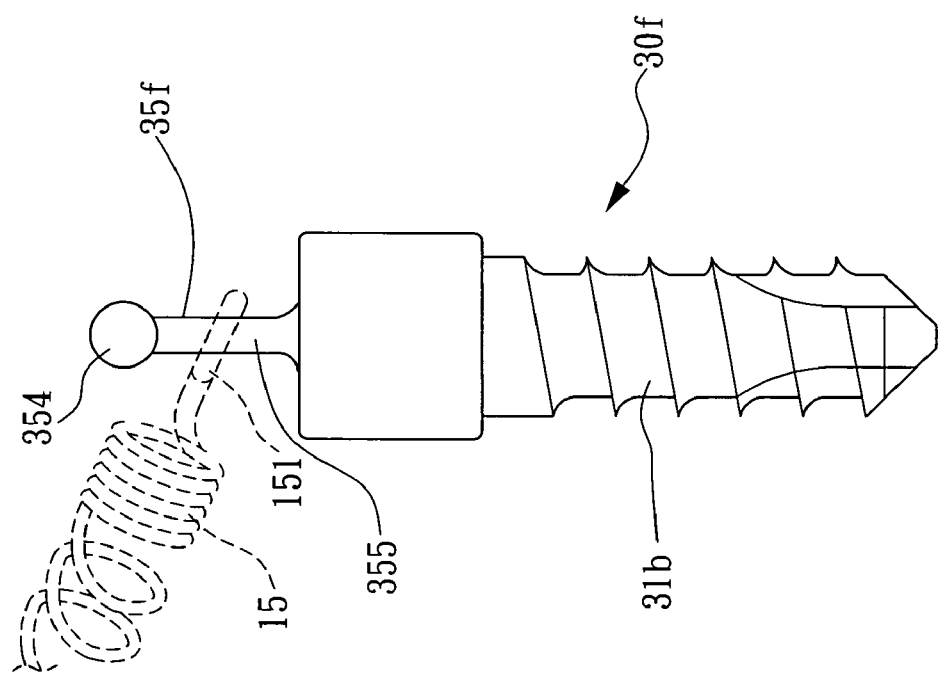
FIG. 9C is the seventh preferred embodiment for the screw device according to the invention for orthodontic treatment.

FIG. 9C is the seventh preferred embodiment for the screw device according to the invention for orthodontic treatment. In this preferred embodiment, most elements of the screw 30f are same as those of the embodiment shown in FIG. 9B, so a repetitious description is skipped herein. The only one different point is that the head part 35f of the screw 30f is straight rod 355 having a ball head 354 located at the top end of the head part. The ball head 354 has a diameter larger than which of the rod 355 of the head part 35f so as to substantially make the rod 355 to be the neck part of the screw 30f.

Figure 10:
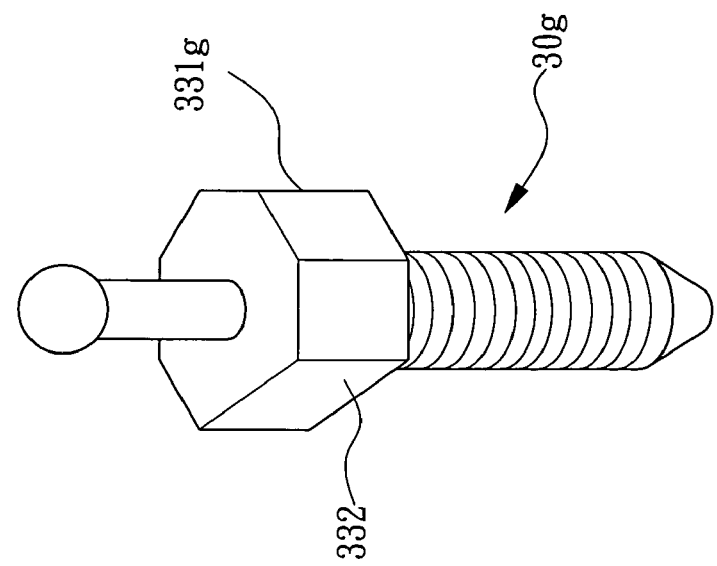
FIG. 10 is the tenth preferred embodiment for the screw device according to the invention for orthodontic treatment.

FIG. 10 is the tenth preferred embodiment for the screw device according to the invention for orthodontic treatment. In this preferred embodiment, most elements of the screw 30g are same as those of the embodiment shown in FIG. 9C, so a repetitious description is skipped herein. The only one different point is that the contour of the platform part 33g of the screw 30g is a polygon contour 331g having a binding area 332 formed at a side portion of the polygon contour 331g of the platform part 33g. The binding area 332 has an area relatively bigger than other side parts of the polygon contour 331g and can be attached with an additional component (not shown in this figure) choosing by the operator (doctor) for assisting orthodontic treatment.

FIG. 11 is the eleventh preferred embodiment for the screw device according to the invention for orthodontic treatment. In this preferred embodiment, most elements of the screw 30h are same as those of the embodiment shown in FIG. 10, so a repetitious description is skipped herein. The only one different point is that the binding area 332h of the platform part 33h of the screw 30h is attached with an orthodontic bracket 334 which is similar to the prior-art orthodontic bracket 14 shown in FIG. 1.

FIG. 12 is the twelfth preferred embodiment for the screw device according to the invention for orthodontic treatment. In this preferred embodiment, most elements of the screw 30i are same as those of the embodiment shown in FIG. 11, so a repetitious description is skipped herein. The only one different point is that the binding area 332i of the screw 30i is attached with a component 335 which has an elongated slot 335l formed adjacent to the binding area 332i. Therefore, the elongated slot 335l substantially forms a through hole for allowing the orthodontic archwire to pass through. In addition, the head part 35i of the screw 30i shown in FIG. 12 is a reversed L-shaped structure which is similar to the one shown in FIGS. 9A and 9B.

FIG. 13 is the thirteenth preferred embodiment for the screw device according to the invention for orthodontic treatment. In this preferred embodiment, most elements of the screw 30j are same as those of the embodiment shown in FIG. 11, so a repetitious description is skipped herein. The only one different point is that the binding area 332j of the screw 30j is attached with a component 336 which has an elongated slot 336*l* formed on a surface away from to the binding area 332*j*. The cut section view of the slot 336*l* is a circle having a diameter similar of slightly larger than which of the orthodontic archwire (not shown in this figure). Therefore, the elongated slot 336*l* can allow the orthodontic archwire to pass therethrough. However, it is noted that the cut section view of the slot 336*l* can also be a rectangular shape as which shown in FIG. 12.

Figure 15:
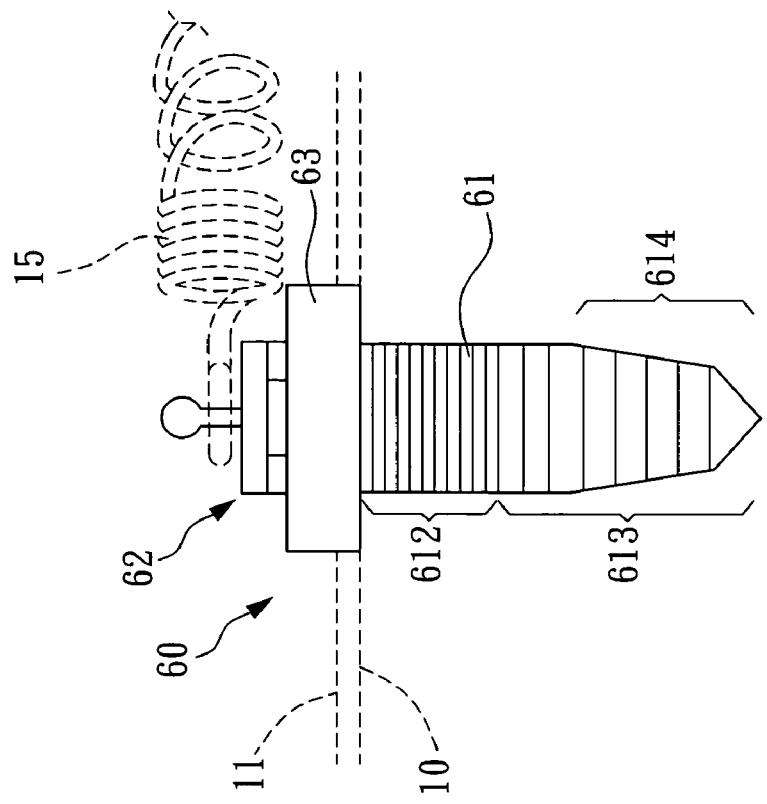
FIG. 15 is a schematic drawing showing the screw device of FIG. 14 being fixed on the maxilla (or mandible) for orthodontic treatment.
Figure 14:
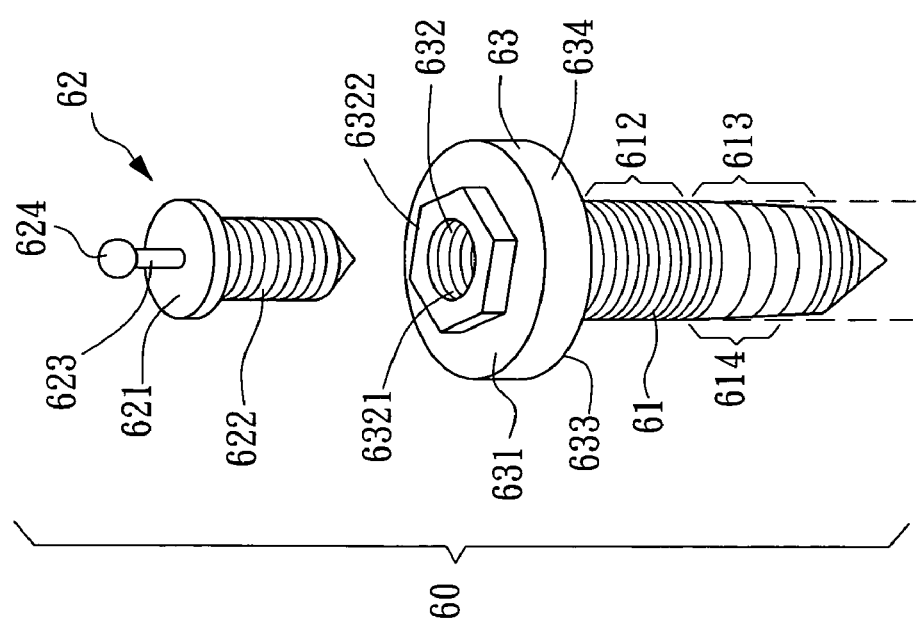
FIG. 14 is the fourteenth preferred embodiment for the screw device according to the invention for orthodontic treatment.

Please refer to FIG. 14 and FIG. 15. FIG. 14 is the fourteenth preferred embodiment for the screw device according to the invention for orthodontic treatment. FIG. 15 is a schematic drawing showing the screw device of FIG. 14 being fixed on the maxilla (or mandible) for orthodontic treatment.

As shown in FIG. 14 and FIG. 15, the fourteenth preferred embodiment of the screw device 60 in accordance with the present invention comprises: a screw-body part 61, a platform part 63 and a head part 62. The screw-body part 60 has a diameter with external threads extending a length. The platform part 63 is axially aligned and integrally formed with the screw-body part 61 to be a single element. The head part 62 is separately manufactured and is an independent element.

In this preferred embodiment, the external threads of the screw-body part 61 are slightly loosened at a portion 613 away from the platform part 63 and are relatively concentrated at another portion 612 near to the platform part 63. In addition, the screw-body part 61 is tapered at a section 614 away from the platform part 63. In one embodiment, the tapered section 614 of the screw-body part 61 has a tapering angle of around 2~10 degrees. By such arrangement, the user (for example, a dentist) will be easy to operate at the beginning when he/she starts screwing the screw device 60 into an object (for example, the maxilla or mandible of a patient). It is because the bottom tip (i.e., section 614) of the screw-body part 61 is narrower and the threads on that portion 613 are relatively loosened, such that the user does not need much effort/strength to screw it. When the user is about to screw the entire screw-body part 61 into the object, the gradually enlarged diameter and concentrated threads (at portion 612) of the screw-body part 61 will provide more tightened and secured fixing result. Of course, the user will need relatively more effort/strength to screw it when the top portion 612 of the screw-body part 61 entering the object. The other advantage for designing the screw-body part 61 with loosened threads and tapered end is that, since the maxilla/mandible of human includes a relatively fragile inner structure and a relatively hard and firm outer structure. The loosened threads and tapered end of the screw-body part 61 can prevent the fragile inner structure of the maxilla/mandible being damaged, while a firm fixing result can still be obtained when the screw-body part 61 is almost entirely screwed into the maxilla/mandible. In addition, the outer surface of the screw-body part 61 (e.g. surfaces of threads) can be roughened to increase friction between the screw-body part 61 and the object (e.g. the maxilla or mandible), such that the screw device 60 of the present invention can be fixed on the object even firmer. Methods for roughening the surfaces of threads include chemical etching and other conventional techniques. Conventional HA particles can also be applied on the surfaces of threads to improve the biointegration effect.

The platform part 63 further comprises a flat top plane 631, a first mating structure 632, a flat bottom plane 633 and an outer periphery 634. In this embodiment, the platform part 63 has a width larger than the width of the screw-body part 61 and the width of the head part 62. The outer periphery 634 is a smooth surface without threads thereon. The shape of the outer periphery 634 can be either round shaped as shown in FIG. 14 or polygon shaped (i.e., being a polygon from the top view thereof). The flat top plane 631 is perpendicular to the screw-body part 61. The first mating structure 632 is formed on the flat top plane 631 and comprises a screw hole 6321 and a nut contour 6322. The screw hole 6321 is for fixing the head part 62. The nut contour 6322 allows the user to use a tool to screw the screw-body part 61 into the object. The flat bottom plane 633 is adjacent to the top end of the screw-body part 61 and is perpendicular to the screw-body part 61, such that when the screw-body part 61 is entirely screwed into the object, the bottom plane 633 will contact a surface of the object (maxilla/mandible 10), as which shown in FIG. 15. As a result, not only the screw device can be fixed firmly, but also the gingiva 11 can recover rapidly and beautifully. Of course, it is also possible for a user (dentist) not to screw the entire screw-body part 61 into the object (maxilla/mandible 10). In this circumstance, there will be a gap between the bottom plane 633 and the object (maxilla/mandible 10). However, since the bottom plane 633 is a flat surface and the outer periphery 634 is a smooth surface, they can still help the gingiva 11 to recover well.

The head part 62 is detachable from the platform part 63 and further comprises a flat cap 621, a second mating structure 622 and an accessory member 623. The second mating structure 622 is formed on a bottom side of the flat cap 62. The second mating structure 622 is capable of engaging with the first mating structure 632 so as to fix the head part 62 onto the platform part 63. In this preferred embodiment, the second mating structure 622 is a screw. The accessory member 623 is formed on a top side of the flat cap 621 for assisting orthodontic treatment. The accessory member 623 is exposed outside of the platform part 63 when the second mating structure 622 engages with the first mating structure 632, such that operations of orthodontic treatment are possible to be performed on the accessory member 623. In the preferred embodiment, the accessory member 623 is formed as a rod-like neck with a uniform width. The neck (accessory member 623) is axially aligned with the screw-body part 61 and extends outwardly from the top side of the flat cap 621 at a first end thereof. The neck (accessory member 623) is configured to removably hook one end of the spring 15. A ball head 624 is located at the top end of the accessory member 623. The ball head 624 has a diameter larger than which of the neck so as to prevent the spring 15 from dropping. The reason why the rod-like neck is axially aligned with the screw-body part 61 and extends outwardly from the top side of the flat cap 621 is that, the thickness of the platform part 63 can act as a protector to prevent the spring 15 from damaging the tissues of the gingiva 11.

FIG. 16A~16H are some preferred embodiments of the head parts 62*a*~62*h* which can be fixed to the platform part 63 and screw-body part 61 of the present invention. Because the head part 62 of the present invention is detachable and changeable, it is possible to design various types of head parts 62*a*~62*h* to mate with the same type of platform part 63 and screw-body part 61 so as to achieve different purposes of orthodontic treatments. Flexibility and convenience for using the screw device 60 are increased. In the mean time, only one type of platform part 63 and screw-body part 61 is needed to be manufactured, thus cost to make screw devices with different functions is decreased. As shown in FIG. 16A, the accessory member 623*a* of the head part 62*a* is formed as an L-shaped structure. In FIG. 16B, the accessory member 623*b* of the head part 62*b* is formed as a hook shaped structure. In FIG. 16C, the accessory member 623c of the head part 62c is a concave formed on the top surface of the head part 62c. The concave (623c) can be used to fill with adhesive to attach an additional component (not shown) for orthodontic treatment as required, for example, an orthodontic bracket or etc. In FIG. 16D, there is no accessory member being formed on the head part 62d, such that the top surface of the flat cap 621d is a plane. User (dentist) can attach an additional component on the top surface of the flat cap 621d if required. In FIG. 16E, the accessory member 623e of the head part 62e is an orthodontic bracket for accommodating an orthodontic archwire (not shown). In FIG. 16F, the accessory member 623f of the head part 62f is a rod-like neck as which shown in FIG. 14. However, the flat cap 621f of this embodiment is thicker and is formed with a rectangular through hole 66 for allowing an orthodontic archwire to pass therethrough. In FIG. 16G, the accessory member 623g of the head part 62g is a cubic having a plurality of flat side surfaces 623l. An additional component, such like an orthodontic bracket 67, can be adhered to one of the flat side surfaces 623l to assist orthodontic treatment. In FIG. 16H, the accessory member 623h of the head part 62h is a cubic having a rod-like neck 68 formed on a side surface thereof for hooking a spring. The cubic is further formed with a round through hole 69 for allowing an orthodontic archwire to pass therethrough.

Figure 17:
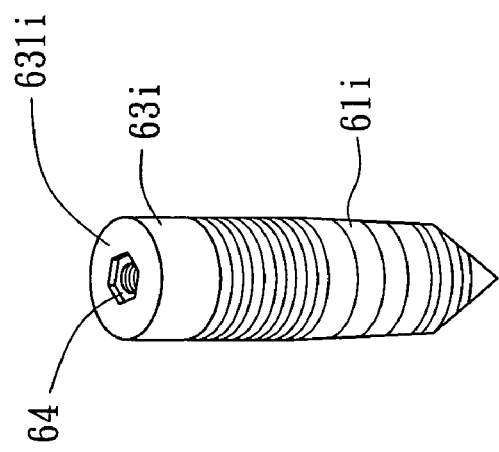
FIG. 17 is another preferred embodiment of the screw-body part in accordance with the present invention.

FIG. 17 is another preferred embodiment of the screw-body part 61i and platform part 63i in accordance with the present invention. In this embodiment, the platform part 63i has a diameter equal to which of the screw-body part 61i. In addition, the flat top plane 631i of the platform part 63i is formed with a nut-shaped bore 64 for allowing a tool, such like a driver, to mate therewith.

Figure 18:
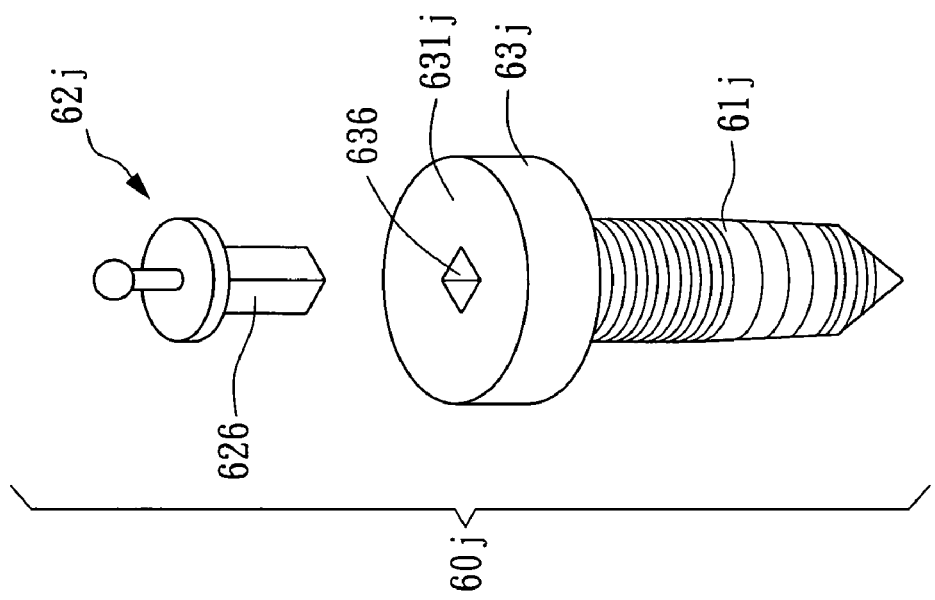
FIG. 18 is the fifteenth preferred embodiment of the screw device according to the present invention.

FIG. 18 is the fifteenth preferred embodiment of the screw device 60j according to the present invention. In this embodiment, the first mating structure is a polygon shaped bore 636 formed on the flat top plane 631j of the platform part 63j. The polygon shaped bore 636 is aligned with the screw-body part 61j. In addition, the second mating structure of the head part 62j is a polygon shaped pillar 626 which can be plugged into and fixed firmly with the polygon shaped bore 636 by adhesive.

Figure 19:
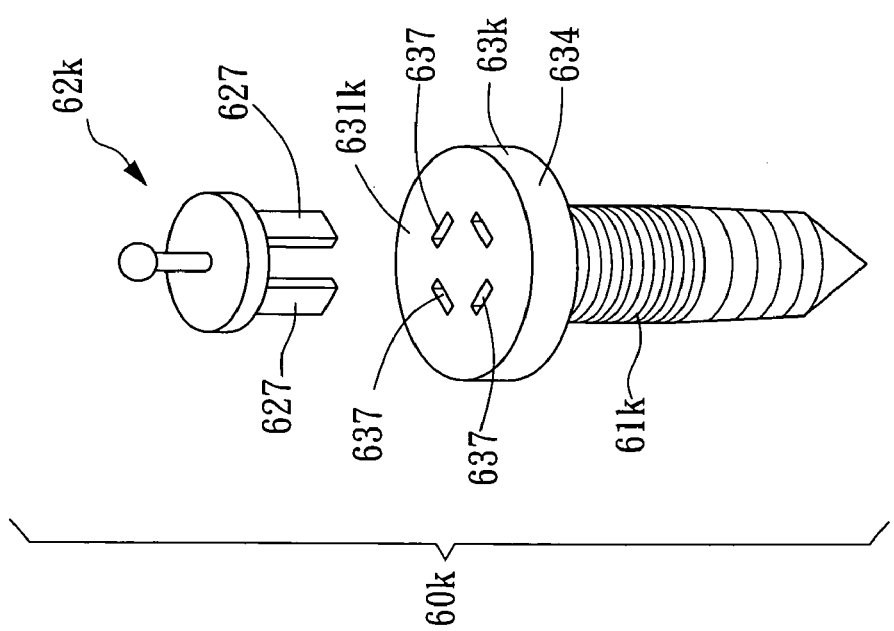
FIG. 19 is the sixteenth preferred embodiment of the screw device according to the present invention.

FIG. 19 is the sixteenth preferred embodiment of the screw device 60k according to the present invention. In this embodiment, the first mating structure includes a plurality of sockets 637 formed on the flat top plane 631k of the platform part 63k. The second mating structure of the head part 62k is a plurality of plugs 627 which are so shaped and positioned that they can be plugged into and fixed firmly with the sockets 637 by adhesive.

Figure 20:
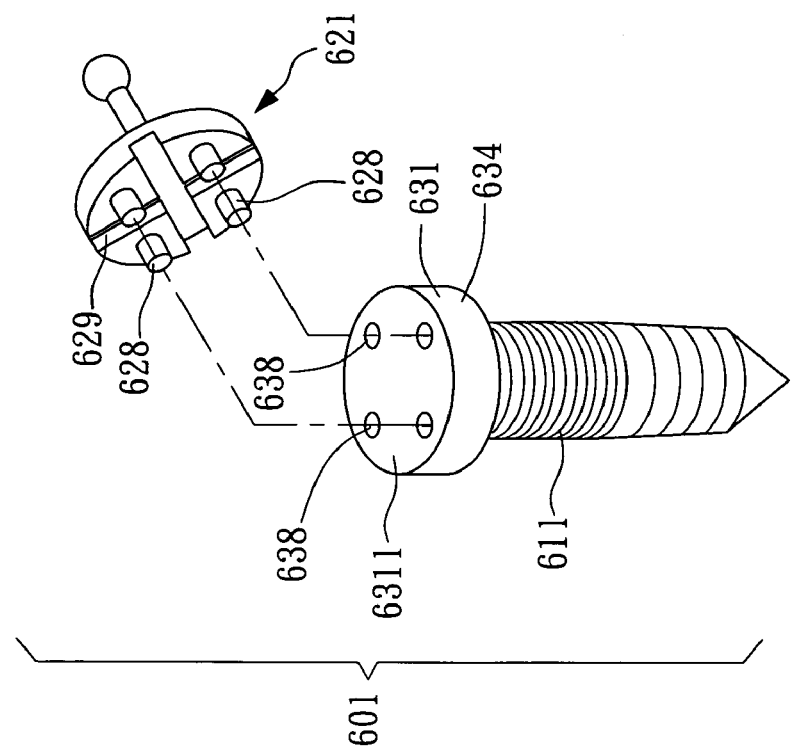
FIG. 20 is the seventeenth preferred embodiment of the screw device according to the present invention.

FIG. 20 is the seventeenth preferred embodiment of the screw device 60l according to the present invention. In this embodiment, the first mating structure includes a plurality of pin holes 638 formed on the flat top plane 631l of the platform part 63l. The second mating structure of the head part 62l is a plurality of pins 628 which are so shaped and positioned that they can be plugged into and fixed firmly with the sockets 638 by adhesive. In addition, the head part 62l is formed with a crisscross-shaped rectangular groove 629 on a surface thereof facing the flat top plane 631l of the platform part 63l. Such that, when the head part 62l is fixed to the platform part 63l, the crisscross-shaped rectangular groove 629 substantially becomes two rectangular through holes (intersecting with each other) for allowing the orthodontic archwire to pass therethrough.

Although the present invention has been described with reference to a preferred embodiment, it should be appreciated that various modifications and adaptations can be made without departing from the scope of the invention as defined in the claims.

What is claimed is:

1. A screw device for orthodontic treatment comprising:
   a screw-body part having a diameter with external threads extending a length wherein the screw-body part is tapered at a section away from a platform part and the tapered section of the screw-body part has a tapering angle of 2~10 degrees, and the external threads of the screw-body part are slightly loosened at a portion away from the platform part and relatively concentrated at another portion near the platform part;
   the platform part axially aligned and integrally formed with the screw-body part, the platform part having:
      a flat top plane perpendicular to the screw-body part;
      a first mating structure formed on the flat top plane; and
      an outer periphery being a smooth surface without threads thereon; and
   a head part which is detachable from the platform part, the head part having:
      a flat cap;
      a second mating structure formed on a bottom side of the flat cap, said second mating structure being capable of engaging with the first mating structure so as to fix the head part on the platform part; and
      an accessory member formed on a top side of the flat cap for assisting orthodontic treatment and comprising a swirl-shaped structure of an arc-shaped wire wound at least 360 degrees;
   wherein the accessory member is exposed outside of the platform part when the second mating structure engages with the first mating structure.

2. The screw device for orthodontic treatment according to claim 1, wherein the platform part has a width larger than the width of the screw-body part and the head part.

3. The screw device for orthodontic treatment according to claim 2, wherein the platform part further has a flat bottom plane adjacent to one end of the screw-body part and perpendicular to the screw-body part, such that when the screw-body part is screwed into an object the bottom plane will be contacting a surface of the object.

4. The screw device for orthodontic treatment according to claim 1, wherein the first mating structure is a screw hole, and the second mating structure is a screw.

5. A screw device for orthodontic treatment comprising:
   a screw-body part having a diameter with external threads extending a length wherein the screw-body part is tapered at a section away from the platform part, said tapered section of the screw-body part has a tapering anale of 2~10 degrees and the external threads of the screw-body part are slightly loosened at a portion away from a platform part and relatively concentrated at another portion near the platform part;
   the platform part axially aligned and integrally formed with the screw-body part, the platform part having a width larger than the width of the screw-body part and a head part and comprising:
      a flat top plane perpendicular to the screw-body part;
      a flat bottom plane adjacent to one end of the screw-body part and perpendicular to the screw-body part, such that when the screw-body part is screwed into an object the bottom plane will be contacting a surface of the object;
      a first mating structure formed on the flat top plane; and
      an outer periphery being a smooth surface without threads thereon; and a the head part which is detachable from the platform part, the head part further having:
   a flat cap;
   a second mating structure formed on a bottom side of the flat cap, said second mating structure being capable of engaging with the first mating structure so as to fix the head part on the platform part; and
   an accessory member formed on a top side of the flat cap for assisting orthodontic treatment;
wherein the accessory member is exposed outside of the platform part when the second mating structure engages with the first mating structure.

6. The screw device for orthodontic treatment according to claim 5, wherein the first mating structure is a screw hole, and the second mating structure is a screw.

7. The screw device for orthodontic treatment according to claim 5, wherein the accessory member further comprises a neck with a uniform width, the neck is axially aligned with the screw-body part and extends outwardly from the top side of the flat cap at a first end thereof, the neck is configured to removably hook one end of a spring, thickness of the platform part determines the distance between the spring and the bottom plane of the platform part.

8. A screw device for orthodontic treatment capable to be used with an orthodontic spring, said screw device comprising:
   a screw-body part having a diameter with external threads extending a length;
   a platform part axially aligned and integrally formed with the screw-body part, the platform part having:
      a flat top plane perpendicular to the screw-body part;
      a first mating structure formed on the flat top plane: and
      an outer periphery being a smooth surface without threads thereon; and
   a head part connected on the flat top plane of the platform part wherein the head part is detachable from the platform part and forming a crisscross-shaped rectangular groove on a surface thereof facing the flat top plane of the platform part, such that when the head part is connected to the platform part, the crisscross-shaped rectanglar groove substantially becomes two rectangular through holes intersecting with each other for allowing an orthodontic archwire to pass therethrough, and the head part comprises:
      a second mating structure for engaging with the first mating structure, and an accessory member for assisting orthodontic treatment,
   wherein the accessory member is exposed outside of the platform part and is at least capable of hooking the orthodontic spring in a removable manner.

9. The screw device for orthodontic treatment according to claim 8, wherein the screw-body part is tapered at a section away from the platform part, said tapered section of the screw-body part has a tapering angle of 2~10 degrees.

10. The screw device for orthodontic treatment according to claim 8, wherein the external threads of the screw-body part are slightly loosened at a portion away from the platform part and relatively concentrated at another portion near to the platform part.

11. The screw device for orthodontic treatment according to claim 8, wherein the platform part has a width lager than the width of the screw-body part and the head part, the platform part further comprises a flat bottom plane adjacent to one end of the screw-body part and perpendicular to the screw-body part, such that when the screw-body part is screwed into an object the bottom plane will be contacting a surface of the object.

12. The screw device for orthodontic treatment according to claim 11, wherein the accessory member further comprises a neck with a uniform width, the neck is axially aligned with the screw-body part and extends outwardly from the top side of the flat cap at a first end thereof, the neck is configured to removably hook one end of a spring, thickness of the platform part determines the distance between the spring and the bottom plane of the platform part.

* * * * *